(12) United States Patent
Gregory et al.

(10) Patent No.: US 11,717,615 B2
(45) Date of Patent: Aug. 8, 2023

(54) COMMUNICATION ACCESSORY FOR A DRUG DELIVERY DEVICE

(71) Applicant: MannKind Corporation, Danbury, CT (US)

(72) Inventors: Christopher Gregory, Hopkinton, MA (US); Geoffrey Jenkins, Dartmouth, MA (US); Matthew Johnson, Boylston, MA (US)

(73) Assignee: Mannkind Corporation, Danbury, CT (US)

( * ) Notice: Subject to any disclaimer, the term of this patent is extended or adjusted under 35 U.S.C. 154(b) by 747 days.

(21) Appl. No.: 16/627,577

(22) PCT Filed: Jul. 13, 2018

(86) PCT No.: PCT/US2018/042079
§ 371 (c)(1),
(2) Date: Dec. 30, 2019

(87) PCT Pub. No.: WO2019/014588
PCT Pub. Date: Jan. 17, 2019

(65) Prior Publication Data
US 2020/0147312 A1  May 14, 2020

Related U.S. Application Data

(60) Provisional application No. 62/532,763, filed on Jul. 14, 2017.

(51) Int. Cl.
*A61M 5/31* (2006.01)
*A61M 5/315* (2006.01)
*G16H 20/17* (2018.01)

(52) U.S. Cl.
CPC .......... *A61M 5/3158* (2013.01); *G16H 20/17* (2018.01); *A61M 2005/3125* (2013.01);
(Continued)

(58) Field of Classification Search
CPC .. A61M 2005/206; A61M 2005/14256; A61M 5/14248; A61M 2005/14252
See application file for complete search history.

(56) References Cited

U.S. PATENT DOCUMENTS

| | | | |
|---|---|---|---|
| 8,708,957 B2 | 4/2014 | Jespersen et al. | |
| 2002/0169439 A1 | 11/2002 | Flaherty | |

(Continued)

FOREIGN PATENT DOCUMENTS

| | | |
|---|---|---|
| WO | 2016029758 A1 | 3/2016 |
| WO | 2016041867 A1 | 3/2016 |
| WO | 2017071983 A1 | 5/2017 |

OTHER PUBLICATIONS

International Search Report dated Nov. 14, 2018 for International PCT Patent Application No. PCT/US2018/042079, 4 pages.

(Continued)

*Primary Examiner* — William R Carpenter
(74) *Attorney, Agent, or Firm* — Morgan, Lewis & Bockius LLP

(57) ABSTRACT

A medicament delivery assembly comprises a delivery device configured to deliver medicament to a user, a communication accessory releasably coupled to the delivery device, and one or more sensors configured to sense a condition of the delivery device. The communication accessory may be configured to receive a first signal from the one or more sensors assembly and to send a second signal to an external device.

25 Claims, 12 Drawing Sheets

(52) U.S. Cl.
CPC ............... *A61M 2205/3306* (2013.01); *A61M 2205/3317* (2013.01); *A61M 2205/3553* (2013.01); *A61M 2205/3561* (2013.01)

(56) References Cited

U.S. PATENT DOCUMENTS

| | | | |
|---|---|---|---|
| 2008/0312604 A1* | 12/2008 | Boesen | A61M 5/2033 604/207 |
| 2010/0274202 A1* | 10/2010 | Hyde | A61M 5/3287 606/213 |
| 2011/0092915 A1* | 4/2011 | Olson | A61M 5/3243 604/198 |
| 2011/0166512 A1* | 7/2011 | Both | A61M 5/14248 604/152 |
| 2011/0306929 A1* | 12/2011 | Levesque | A61M 5/3234 604/150 |
| 2013/0274655 A1* | 10/2013 | Jennings | A61M 5/3213 604/152 |
| 2014/0354998 A1* | 12/2014 | Bock | A61M 5/31 356/445 |
| 2015/0144793 A1* | 5/2015 | Whalley | G01F 13/00 250/357.1 |
| 2016/0213856 A1 | 7/2016 | Becton | |
| 2017/0119969 A1 | 5/2017 | McCullough et al. | |
| 2017/0368260 A1* | 12/2017 | McCullough | A61M 5/14248 |

OTHER PUBLICATIONS

Written Opinion dated Nov. 14, 2018 for International PCT Patent Application No. PCT/US2018/042079, 7 pages.

\* cited by examiner

COMMUNICATION ACCESSORY FOR A DRUG DELIVERY DEVICE

CROSS-REFERENCE TO RELATED APPLICATIONS

This application is a U.S. National Stage Application that claims the benefit of International Patent Application No. PCT/US2018/042079 filed Jul. 13, 2018, which claims the benefit of U.S. Provisional Patent Application No. 62/532,763 filed Jul. 14, 2017 entitled "Communication Accessory for a Drug Delivery Device", each of which is incorporated by reference herein in its entirety.

FIELD OF THE INVENTION

The present invention generally relates to a communication accessory for a drug delivery device.

BRIEF SUMMARY OF THE INVENTION

In one embodiment, a medicament delivery assembly comprises a delivery device configured to deliver medicament to a user. The medicament delivery assembly may include a communication accessory releasably coupled to the delivery device and one or more sensors configured to sense a condition of the delivery device. The communication accessory may be configured to receive a first signal from the one or more sensors and to send a second signal to an external device.

The delivery device may include a medicament chamber configured to hold a medicament, a plunger configured to move relative to the medicament chamber to expel the medicament from the medicament chamber, and a needle coupled to the medicament chamber. Medicament may flow through the needle from the medicament chamber to the user. The one or more sensors may be configured to sense a volume of medicament in the medicament chamber.

The plunger may be moveable relative to the medicament chamber and the one or more sensors may be configured to sense a position of the plunger in the medicament chamber. The needle may be moveable relative to the delivery device from a retracted position to an extended position and the one or more sensors may be configured to sense a position of the needle.

In a further embodiment, the delivery device may include a needle deploy button configured to move the needle between a retracted position and an extended position. The one or more sensors may include a sensor configured to sense activation of the needle deploy button. The delivery device may include a bolus delivery button and the one or more sensors may be configured to sense activation of the bolus delivery button. The communication accessory may include a processor configured to determine at least one of a number of boluses delivered, a number of boluses remaining, delivery of a dose of medicament from the medicament chamber, and a number of deses of medicament remaining in the medicament chamber.

The external device may include a processor configured to determine at least one of a number of boluses delivered, a time when the bolus was delivered, a quantity of boluses remaining, a volume of medicament delivered from the medicament chamber, a number of doses delivered from the medicament chamber, a number of doses of medicament remaining in the medicament chamber, and an expected time of medicament chamber emptying based on the second signal. The delivery device may be non-electronic. Each of the one or more sensors may be configured to sense one of a plurality of conditions of the delivery device. The external device may include a software application configured to display indicia related to the condition sensed by the one or more sensors. The one or more sensors may be part of a sensor assembly. The delivery device may be a non-electronic delivery device and the one or more sensors may include an electronic sensor configured to sense a condition of the non-electronic delivery device.

The delivery device may be selected from a plurality of delivery device models and the sensor assembly may be configured to sense the model of the selected delivery device. The one or more sensors may include at least one of a magnetic sensor, a capacitive sensor, a pushbutton switch, a membrane switch, a molded elastomeric switch, a tactile switch, and an optical sensor. The communication accessory may include memory and the communication accessory may be configured to store the first signal in the memory as a saved signal. The communication accessory may be configured to send the second signal to the external device via a wireless connection.

A medicament delivery assembly kit may include one of a plurality of delivery devices, one or more sensors configured to sense a condition of each of the plurality of delivery devices, and the communication accessory. The communication accessory may be configured to releasably couple to each of the plurality of delivery devices. The delivery device may be an electronic delivery device that does not transfer use information.

In a further embodiment, a medicament delivery assembly includes a non-electronic delivery device configured to deliver medicament to a user. The delivery device may include a medicament chamber configured to hold a medicament, a plunger configured to move relative to the medicament chamber to expel the medicament from the medicament chamber, a needle coupled to the medicament chamber, the needle moveable from a retracted position to an extended position. Medicament may flow through the needle from the medicament chamber to the user when the needle is in the extended position. The delivery device may include a needle deploy button configured to move the needle between the retracted position and the extended position and a bolus delivery button configured to deliver a bolus of medicament to the user through the needle.

The medicament delivery assembly may include a communication accessory releasably coupled to the non-electronic delivery device. The communication accessory may include one or more sensors configured to sense a condition of the delivery device and provide a signal related to the sensed condition. The one or more sensors may include a first sensor configured to sense a position of the needle, a second sensor configured to sense activation of the needle deploy button, and a third sensor configured to sense activation of the bolus delivery button. The communication accessory may be configured to receive at least one signal from the sensor assembly and to send a second signal related to the at least one signal to an external device. The external device may include a software application configured to display indicia related to the condition sensed by the one or more sensors. The software application may be configured to determine at least one of a model of the delivery device, a number of boluses delivered by the medicament delivery device, a number of boluses remaining in the medicament delivery device, a volume of medicament delivered from the medicament delivery device, a number of doses of medicament delivered from the medicament delivery device, a volume of medicament remaining in the medicament delivery device, a number of doses of medicament remaining in the medicament delivery device, a time the needle was deployed by the medicament delivery device, and an expected time when a medicament chamber in the medicament delivery device will be empty based on the second signal.

In a further embodiment, a communication accessory comprises a top surface and two opposed sidewalls extending from the top surface, the two opposed sidewalls configured to clip onto corresponding sidewalls of a medicament delivery device. A sensor may be configured to sense a condition of the medicament delivery device. The communication accessory may be configured to releasably couple to the medicament delivery device. The communication accessory may be configured to receive a first signal from the sensor and to send a second signal to an external device. The sensor may be configured to sense at least one of a model of the medicament delivery device, a movement of a bolus delivery trigger, and a battery status of the medicament delivery device. The sensor may be positioned on one of the two opposed sidewalls.

In a further embodiment, the communication accessory includes one or more additional sensors configured to sense at least a second condition of the medicament delivery device. The one or more sensors may be positioned on a bottom surface of the medicament delivery device. The one or more sensors may be generally parallel with one of the two opposed sidewalls. One of the two opposed sidewalls may include a cutout. In a further embodiment, one of the two opposed sidewalls includes a lip adjacent the cutout. In a further embodiment, the communication accessory includes a rear wall and a relief between the rear wall and one of the two opposed sidewalls.

In one embodiment, a communication accessory includes a body and a sensor(s) configured to sense a condition of the medicament delivery device. The communication accessory may be configured to releasably couple to a medicament delivery device. The communication accessory may be configured to receive a first signal from the sensor and to send a second signal to an external device. The communication accessory may be configured to be releasably coupled to a non-electronic medicament delivery device. The external device may include a processor configured to use at least one of the signals from the communication accessory to determine at least the model of the delivery device, one of a number of boluses delivered by the medicament delivery device, a number of boluses remaining in the medicament delivery device, a volume or dose of medicament delivered from the medicament delivery device, a volume or dose of medicament remaining in the medicament delivery device, a time the needle was deployed by the medicament delivery device, and an expected time when a medicament chamber in the medicament delivery device will be empty. The external device may include a software application configured to display indicia related to the condition determined from the communication accessory.

BRIEF DESCRIPTION OF THE SEVERAL VIEWS OF THE DRAWINGS

The foregoing summary, as well as the following detailed description of embodiments of the communication accessory for a drug delivery device, will be better understood when read in conjunction with the appended drawings of an exemplary embodiment. It should be understood, however, that the invention is not limited to the precise arrangements and instrumentalities shown. For example, although not expressly stated herein, features of one or more various disclosed embodiments may be incorporated into other of the disclosed embodiments.

In the drawings.

DETAILED DESCRIPTION OF THE INVENTION

Figure 1:
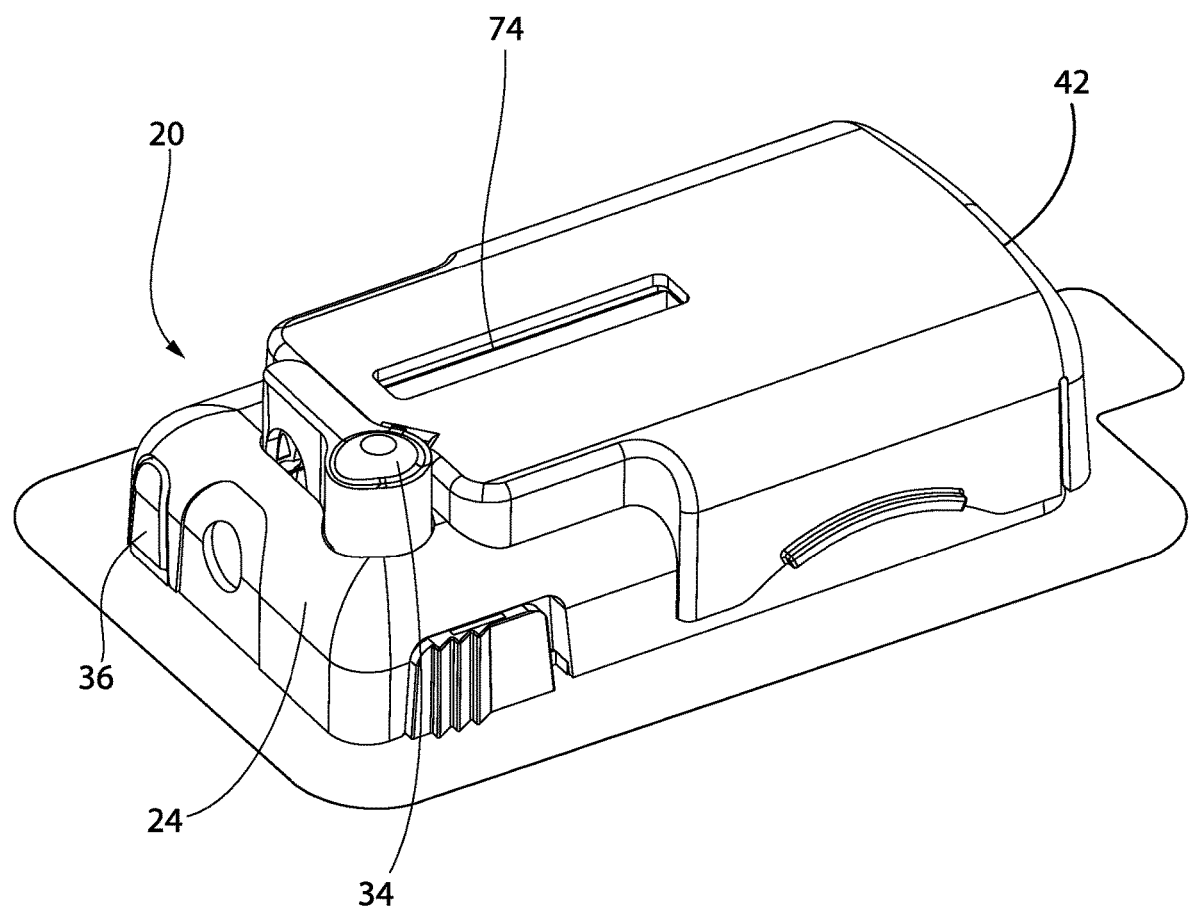
FIG. 1 is a top trimetric view of a communication accessory coupled to a delivery device in accordance with an exemplary embodiment of the present invention.

Ambulatory drug delivery systems may provide a steady supply of drug to a patient at a predetermined rate (i.e., basal delivery) and the periodic delivery of specific volumes of drug on demand (i.e., bolus delivery) or each individually. In an electronically controlled delivery system, the drug delivery may be electronically controlled. Data about the basal and/or bolus delivery may be transmitted to a receiver such as a mobile device through a wired or wireless communication protocol. The data can then be transmitted to another entity such as the clinician's office, remote server, or a data repository.

A non-electronic delivery device, or an electronic delivery device that does not capture use information, cannot transfer the use information to the mobile device and may be of less utility than a device which can capture and/or transfer the use information. The communication accessory described herein may be attached to a non-electronic or non-data collecting electronic fluid delivery device and can detect information about the use of the device and transmit that information to a mobile device for display and communicating.

The information may include the model of the device (and thus flow rate if it is fixed), the status of the delivery needle (if the needle is integrated), the movement of a bolus delivery trigger, and/or information about the communication accessory such as identification, error codes, and battery status. The collecting and transmission of information along with the relative time of the detection of these events allows the determination of when the accessory was placed on the delivery system, the model and basal flow rate of the delivery device, the time of needle deployment, the time of any bolus requests, the time of needle withdrawal, and the time of communication accessory removal.

The collected data may also allow the calculation of the total drug delivered, number of boluses delivered, number of boluses remaining, time since needle deploy, and time until the delivery device is expected to run out of medicament as well as other calculations. These calculations may be done in the accessory and then transmitted to the mobile device. These calculations may be done in the mobile device once the basic information on each event is transmitted to the mobile device. The record of use for the fluid delivery device can be transmitted to the mobile device and stored in a format that will allow other programs to access the data for other processing. The data or a report of the data can be transmitted from the mobile device to other destinations such as a clinician's office, a central data repository, or the manufacturing company for analysis. A user may select where the data is exported to or select permissions to limit who can access the data and if the data is provided anonymously.

Referring to the drawings in detail, wherein like reference numerals indicate like elements throughout, there is shown in FIGS. 1-12 a delivery device, generally designated 20, in accordance with an exemplary embodiment of the present invention.

Figure 2:
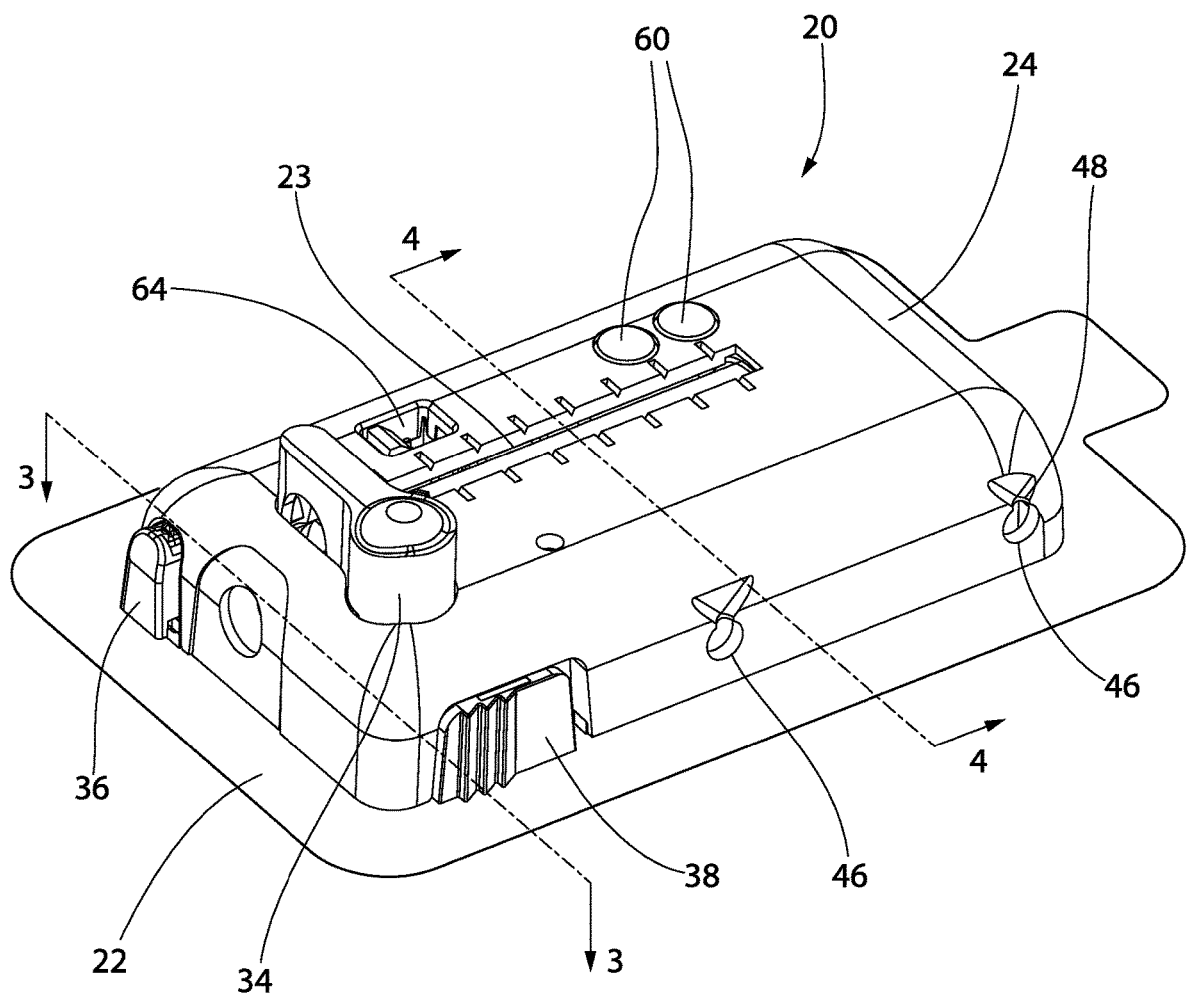
FIG. 2 is a top trimetric view of the delivery device of FIG. 1.

Referring to FIG. 2, the delivery device 20 may be coupled to a user's skin to deliver a substance (e.g., a fluid such as a drug) to a user. The delivery device 20 may be configured to deliver a medicament or drug subcutaneously to a user. The delivery device 20 may include a patch 22 which couples the delivery device 20 to a user's skin. The patch 22 may be an adhesive patch that self-adheres to the user's skin. The delivery device 20 may include a housing 24 coupled to the patch 22.

In one embodiment, the delivery device 20 is a discrete ambulatory insulin delivery pump. Delivery device 20 may be single use, disposable and incapable of reuse. The delivery device 20 may provide therapeutic capability in a small, single use, disposable package and at least some portions can be produced using high volume manufacturing fabrication (e.g., injection molding) and assembly processes, allowing for low cost of goods. Delivery device 20 may be configured for multiple uses by replenishing the medicament in the delivery device. Devices of the invention can be used for a broad range of applications, including, but not limited to, clinical applications (e.g., administration of medicaments, etc.) and biomedical research (e.g., microinjection into cells, nuclear or organelle transplantation, isolation of single cells or hybridomas, etc.). Some devices contemplated for use with the present invention are described in U.S. Pat. Nos. 7,530,968 and 9,101,706, the disclosure of each of which is are incorporated by reference herein in its entirety. In some embodiments, the delivery device is purely mechanical and/or hydraulic. In some embodiments, the delivery device does not include any electronic components.

In one embodiment, the delivery device 20 is a device for dispensing, delivering, or administering fluid or agent to the user or patient. In one embodiment, the fluid is insulin of any type. In other embodiments, the fluid may be, but is not limited to, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) may be delivered using delivery device 20. As used herein "patients" or "user" can be human or non-human animals; the use of delivery device 20 is not confined solely to human medicine, but can be equally applied to veterinarian medicine.

The delivery device 20 may dispense a selected volume of fluid or medicament over a selected period of time (i.e., basal delivery). In one embodiment, the fluid delivery rate is continuously, or near continuously, delivered to the user over the selected period of time.

Figure 3:
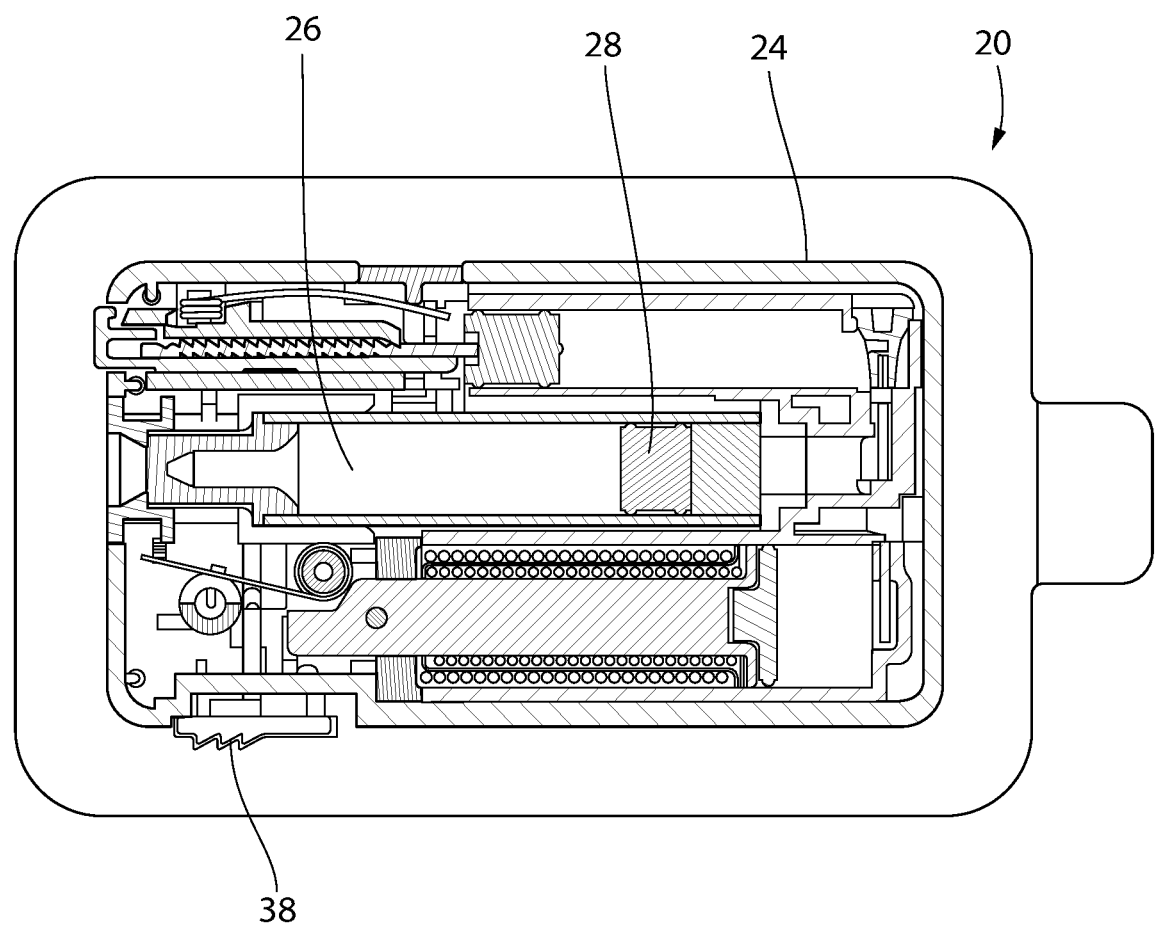
FIG. 3 is a top sectional view of the delivery device of FIG. 2 taken along a plane, the location and direction being indicated by line 3-3 in FIG. 2.
Figure 4:
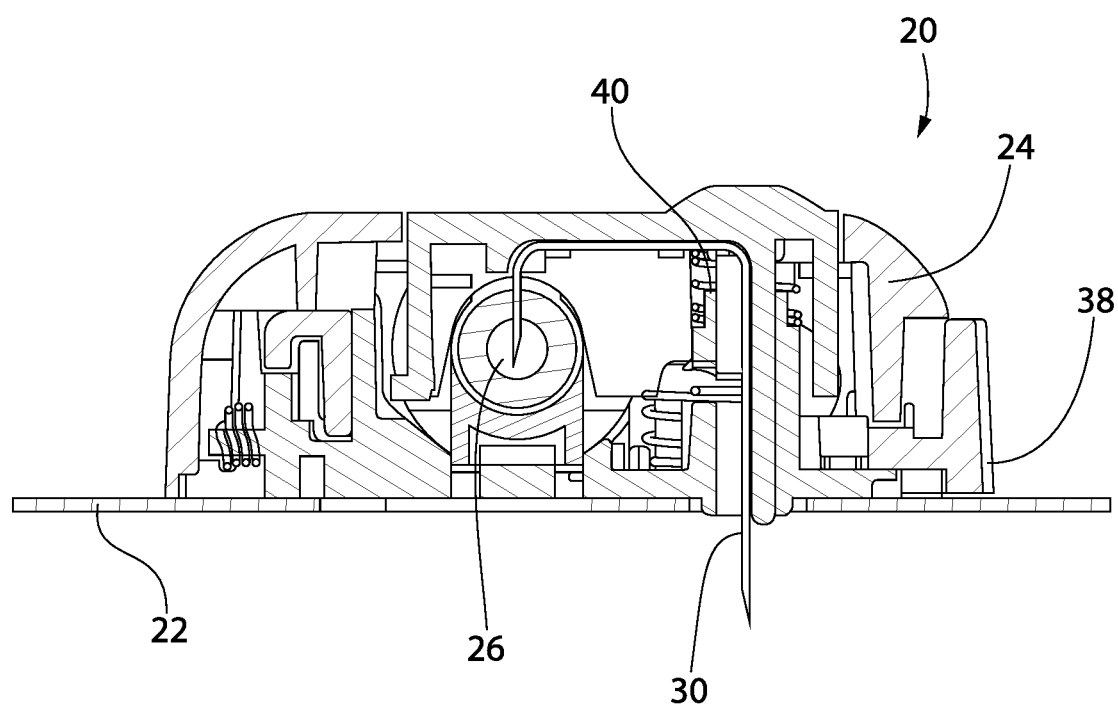
FIG. 4 is a front cross sectional view of the delivery device shown in FIG. 2 taken along a plane, the location and direction being indicated by line 4-4 in FIG. 2.

Referring to FIGS. 2-4, the delivery device 20 may include a medicament chamber 26 within the housing 24. A plunger 28 may be positioned in the medicament chamber 26. The plunger 28 may be moveable within the medicament chamber 26 to expel medicament from the medicament chamber 26 as explained in greater detail below. In one embodiment, the plunger 28 is moved relative to the medicament chamber 26 by a biasing element (e.g., a spring). In another embodiment, the plunger 28 is moved by fluid pressure (e.g., hydraulic fluid) or gas pressure. A needle 30 (best seen in FIG. 4) may be in fluid communication with the medicament chamber 26. The needle 30 may be moveable from a retracted position to an extended position (needle shown in an extended position in FIG. 4). The needle may be configured to deliver medicament from the medicament chamber 26 to the user when the needle 30 is in the extended position. The depth that the needle 30 extends away from the housing 24 when the needle 30 is in the extended position may be selected such that the needle delivers medicament at a desired depth (e.g., subcutaneously or intramuscularly).

Referring to FIG. 1, the delivery device 20 may include a needle deploy button 34. In one embodiment, the needle deploy button 34 is depressible relative to the housing 24. The needle deploy button 34 may be actuated to move the needle 30 from the retracted position toward the extended position wherein the needle 30 extends out of the bottom surface of the delivery device 20, into the user's skin and locks the needle 30 into place for fluid delivery. In one embodiment, the needle deploy button 34 is actuated by depressing the needle deploy button 34 such that the needle deploy button 34 moves from a needle deploy button retracted position to a needle deploy button extended position as the needle moves between the retracted position and the extended position. In one embodiment, the needle deploy button 34 is actuated in a direction generally perpendicular to the bottom surface of the delivery device 20. A needle button cover (not shown) may extend over the needle deploy button 34 before use to protect the needle deploy button 34 from being unintentionally depressed and prematurely deploying the needle 30.

Referring to FIG. 2, the delivery device 20 may include a bolus delivery button 36. Actuating the bolus delivery button 36 may dispense a predetermined volume of medicament from the delivery device 20 to a user. In one embodiment, the bolus delivery button 36 is unlocked by pressing a release catch (not shown) that allows the bolus delivery button 36 to extend out from the delivery device 20. In another embodiment, the bolus delivery button 36 is placed in a ready state by pulling a release pin (not shown) or removing a bolus delivery button cover (not shown). In one embodiment, the bolus delivery button 36 is actuated in a direction generally parallel with the bottom surface of the delivery device 20.

Referring to FIGS. 2-4, the delivery device 20 may include a needle retract button 38. Activating the needle retract button 38 may cause the needle to retract such that the needle point is contained within the housing 24 (e.g., the needle may move from the extended position to the retracted position). The delivery device 20 may include a biasing element 40 and pressing the needle deploy button 34 may cause the biasing element to deform such that when the needle retract button 38 is activated, the needle 30 is retracted into the housing by the biasing element 40. In one embodiment, the biasing element 40 is a spring. In another embodiment, the biasing element 40 is compressed gas within a piston and cylinder assembly. The delivery device 20 may include a window 23 aligned with the medicament chamber 26. The window 23 may allow a user to observe the medicament chamber 26 through the housing 24.

Figure 5:
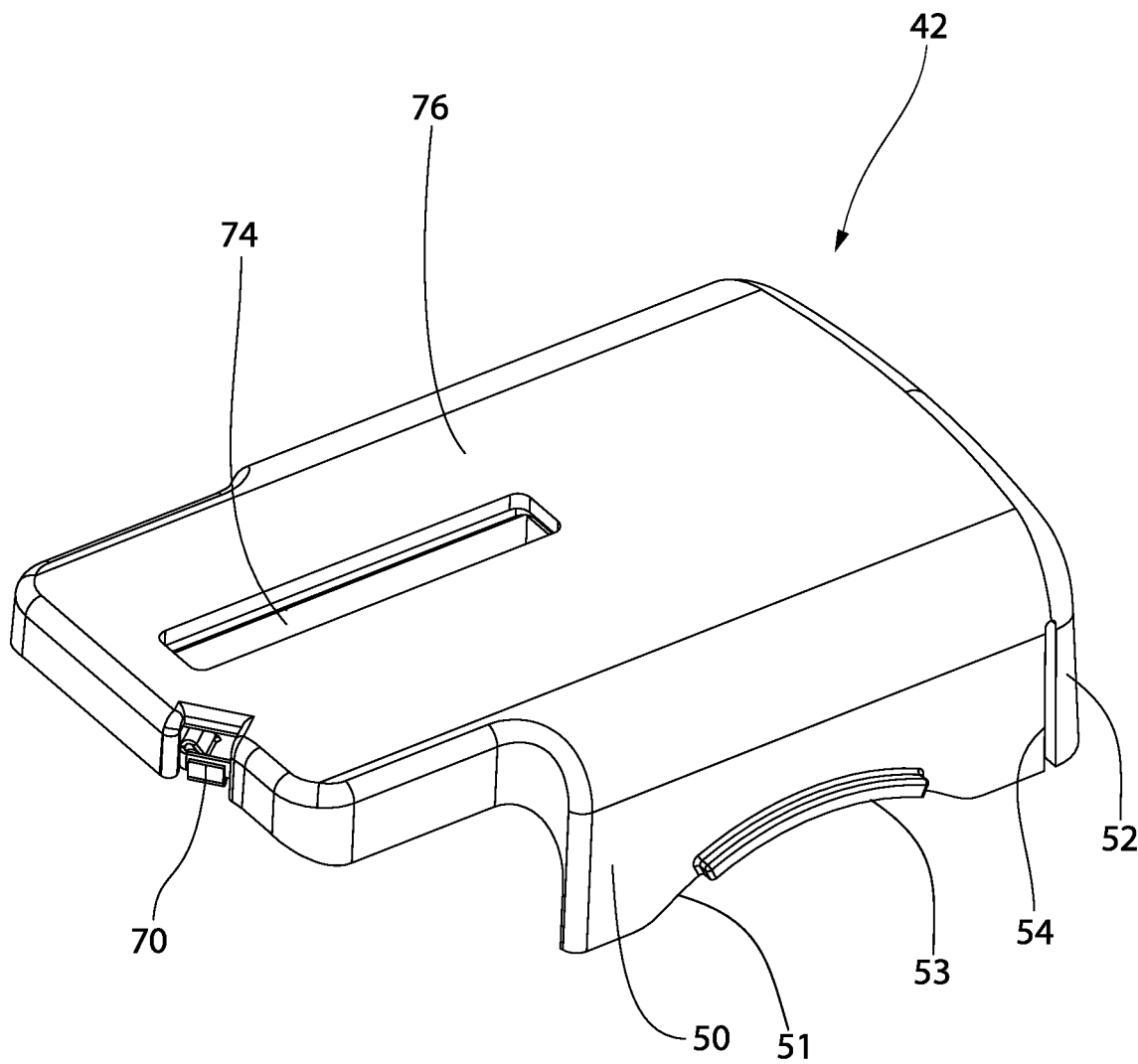
FIG. 5 is a top trimetric view of the communication accessory of FIG. 1.

Referring to FIGS. 1 and 5, a communication accessory 42 may be provided and configured to couple to the delivery device 20. In one embodiment, the communication accessory 42 may be releasably coupled to the delivery device 20. In one embodiment, the communication accessory 42 is releasably coupled to a plurality of delivery devices 20 such that the communication accessory 42 may be reused with different disposable delivery devices 20. In one embodiment, the communication accessory 42 is configured to be reused. In one embodiment, the communication accessory 42 is configured to be usable as long as a battery in the communication accessory maintains sufficient power. The communication accessory 42 may have a life of about 1 month to about 1 year. In one embodiment, the communication accessory 42 is coupled to a disposable delivery device 20 configured to be replaced daily such that the communication accessory is coupled to about 28 to about 365 delivery devices. In one embodiment, the battery in the communication accessory 42 is rechargeable or replaceable and the communication accessory 42 is viable for a longer period of time (e.g., several years) and may be coupled to thousands of delivery devices 20.

In one embodiment, the communication accessory 42 includes one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein. The communication accessory 42 may be configured to communicate information about the delivery device 20 with one or more remote applications, servers, cellular phones, or computers, as explained in greater detail below.

The communication accessory 42 may be used to retro-fit to existing delivery devices. The communication accessory 42 may be sold separately from a delivery device. In some embodiments, a kit may be provided that includes the communication accessory 42 and multiple delivery devices 24. In some embodiments, a kit is provided that includes the communication accessory 42 and five or more delivery devices. In one embodiment, a kit is provided that includes the communication accessory 42 and about five delivery devices 20. In one embodiment, a kit is provided that includes the communication accessory 42 and about ten delivery devices 20. In one embodiment, a kit is provided that includes the communication accessory 42 and about ten delivery devices 20. In one embodiment, a kit is provided that includes the communication accessory 42 and about twenty delivery devices 20. In one embodiment, a kit is provided that includes the communication accessory 42 and about thirty delivery devices 20. In one embodiment, a kit is provided that includes the communication accessory 42 and more than forty delivery devices 20.

Figure 6:
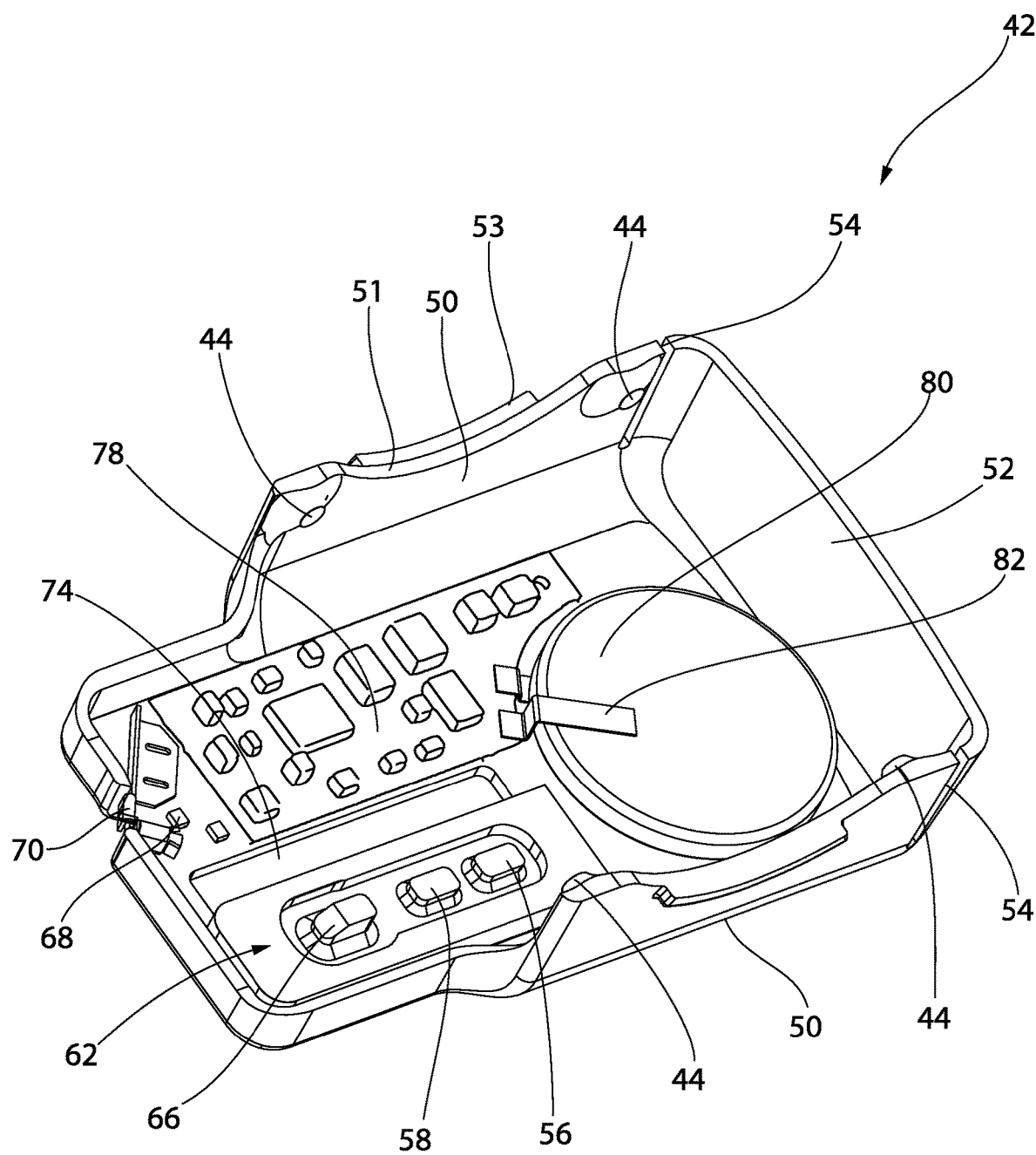
FIG. 6 is a bottom trimetric view of the communication accessory of FIG. 5.

Referring to FIGS. 1, 2, and 6, the communication accessory 42 may include an accessory engagement feature 44 (FIG. 6) configured to engage a housing engagement feature 46 (FIG. 2) to at least temporarily couple the communication accessory 42 to the housing 24 until intentionally released by the user. In one embodiment, the accessory engagement features 44 include one or more protrusions and/or recesses on the interior of the communication accessory 42 and the housing engagement features 46 include corresponding recesses and/or protrusions configured to engage the accessory engagement features 44. In another embodiment, the accessory engagement features 44 and the housing engagement features 46 are apertures configured to receive a connector (e.g., a screw, a bolt, a nail, or a pin). In yet another embodiment, the accessory engagement features 44 and the housing engagement features 46 are magnets or hook and loop fasteners (e.g., Velcro® brand fasteners). The housing engagement feature 46 may include an alignment feature 48 (e.g., a ramp or a slot) configured to align and guide the accessory engagement feature 44 into engagement with the housing engagement feature 46. In one embodiment, the alignment feature 48 is above the housing engagement feature 46 such that the communication accessory 42 may be moved down vertically relative to the housing 24 to engage the accessory engagement feature 44 with the housing engagement feature 46. In another embodiment, the alignment feature 48 is on a side of or below the housing engagement feature 46 such that the communication accessory 42 may slide horizontally or be rotated relative to the housing 24 to couple the communication accessory 42 to the delivery device 20. The communication accessory 42 may be snap-fit onto the delivery device 20.

Referring to FIGS. 5 and 6, the communication accessory 42 may include a body having sidewalls 50 and an end wall 52. The communication accessory 42 may have a concave shape configured to receive at least a portion of the housing 24. The communication accessory 42 may cover the window 23, a bolus delivery button indicator 64, and/or indicator 60 when the communication accessory 42 is coupled to the housing 24. The communication accessory 42 may cover about 50%, about 60%, about 70%, about 80%, about 90%, or about 99% of a top surface of the housing 24 when the communication accessory 42 is coupled to the housing 24.

A relief 54 may be formed where the sidewall 50 meets the end wall 52. The relief 54 may be a cutout or flexible material such that the sidewalls 50 and end wall 52 may move relative to each other as the communication accessory 42 is coupled to the delivery device 20. The sidewalls 50 may be moveable from a relaxed position to an expanded position. The sidewalls 50 may be in the expanded position as the communication accessory 42 is positioned on the housing 24. The sidewalls 50 may be in the relaxed position when the accessory engagement feature 44 is engaged with the housing engagement feature 46. In one embodiment, the end wall 52 assists in properly aligning the communication accessory 42 on the delivery device 20. In another embodiment, the communication accessory 42 does not include an end wall.

The sidewalls 50 may include a portion defining a cutout 51. The cutout 51 may be defined by a sidewall having a radius of curvature of about 0.5 inches, about 0.65 inches, about 0.8 inches, about 1 inch, about 2 inches, about 3 inches, about 4 inches, about 5 inches, or about 6 inches. The sidewall 50 may include a lip 53 that protrudes away from a surface of the sidewall 50. The lip 53 may provide a surface that a user can grip (e.g., with their thumb or finger) to couple or decouple the communication accessory 42 and the housing 24. The lip 53 may have a radius of curvature similar to that of the cutout 51 (e.g., within about 0.25 inches, about 0.5 inches, about 0.75 inches, about 1 inch, about 1.5 inches, or about 2 inches). In some embodiments, the lip 53 is solid. In other embodiments, the lip 53 is a hollow or semi-solid extension from sidewall 50.

An opening 74 may extend through an upper surface 76 of the communication accessory 42. In one embodiment, the opening 74 is unobstructed. In another embodiment, the opening 74 is covered with a transparent material to form a window. The opening 74 may be aligned with the window 23 of the delivery device 20 such that a user may observe the medicament chamber 26 through the opening 74 when the communication accessory 42 is coupled to the delivery device 20. A wall may extend around the opening 74 toward an inside of the accessory 42 to contain liquid potting material, as explained in greater detail below.

Referring to FIGS. 2 and 6, the communication accessory 42 may be configured to detect the presence of the delivery device 20. The communication accessory 42 may be configured to be coupled to a plurality of models of the delivery device. The communication accessory 42 may be configured to sense which of a plurality of models of delivery devices the communication accessory 42 is coupled to. The communication accessory 42 may include a sensor or sensor assembly 62 including at least one sensor to detect which model delivery device the communication accessory 42 has been coupled to. The sensor assembly 62 may include a first sensor 56 and a second sensor 58 to detect the presence or absence of one or more indicators 60 (see FIG. 2).

One or more indicators 60 may be provided on or in the delivery device such that the communication device can sense the one or more indicators and identify the model or configuration of the delivery device 20. In one embodiment, the communication accessory 42 may be configured to couple to any of three delivery device models. In one embodiment, the sensor assembly 62 of the communication accessory 42 includes two binary device sensors, first sensor 56 and second sensor 58, and the delivery device 20 includes two indicators 60 such that the communication accessory may distinguish between four situations, one where no device is attached and which of the delivery device models the communication accessory 42 is coupled to according to the following exemplary schematic:

| First Sensor | No signal | signal | no signal | signal |
|---|---|---|---|---|
| Second Sensor | No signal | no signal | signal | signal |
| Model Detected | No Delivery Device | Model A | Model B | Model C |

In one embodiment, the sensor assembly 62 includes a magnetically sensitive sensor (Hall Effect or reed switch) and the indicator 60 is a magnet. In another embodiment, the sensor assembly 62 includes a capacitive sensor and the indicators 60 are conductive areas. In another embodiment, the sensor assembly 62 includes electrical contacts and the indicators 60 are conductive areas. In another embodiment, the sensor assembly 62 includes pushbutton switches and the indicators 60 are protrusions. In another embodiment, the sensor assembly 62 includes switches and the indicators 60 are recesses. In another embodiment, the sensor assembly 62 includes membrane or elastomeric switches with reversibly displaceable portions that distort under force and electrically connect contacts under the collapsed portions and return to their initial shape breaking contact when the force is removed. In another embodiment, the sensor assembly 62 includes detect micro switches. In another embodiment, the sensor assembly 62 includes tactile switches and the indicators 60 are flexible. In some embodiments, the sensor assembly 62 is configured to generate a first signal indicative of the model of the delivery device which the sensor assembly is coupled to. In some embodiments, the sensor assembly 62 is configured to generate a second signal indicative of a time the needle of the delivery device was deployed.

In one embodiment, one or more of the sensor assembly 62 and the indicators 60 are at least partially coated with a waterproofing material (e.g., Parylene or polyurethane). In one embodiment, at least one of the sensor assembly 62 and the indicators 60 are covered with a hydrophobic coating. In one embodiment, at least one of the sensor assembly 62 and the indicators 60 are covered with a waterproofing membrane molded or formed to allow the switches to be activated through the membrane. In one embodiment, at least one of sensor assembly 62 and the indicators 60 are indirectly actuated by ridged or flexible lever arms that are deflected by contact with indicators 60.

The sensor assembly 62 may include optical sensors and the indicators 60 may be optically detectable indicia (e.g., pigmented areas). The communication accessory 42 may detect the different delivery device models through one sensor (e.g., one of the first sensor 56 and the second sensor 58). In one embodiment, the first sensor 56 is an optical sensor that can distinguish indicia (e.g., a pattern or code) forming the indicator 60 (e.g., a pattern or code). In another embodiment an optical sensor could detect a color pigment or fluorescent emission of a specific wavelength range after excitation from a source in the communication accessory 42.

The sensor assembly 62 may be configured to sense one or more events such as a relative time when the needle is deployed or a relative time when a bolus is delivered. The communication accessory 42 may transmit a signal indicative of these events to an external device. The external device may include a processor that determines at least one of an actual time when the bolus was delivered, the time since a bolus was last delivered, the total doses delivered, and the total doses remaining based on the transmitted signal. The external device may determine a time when the medicament chamber of the delivery device will be empty based on at least one of the time the needle was deployed, the model of the delivery device, and the flow rate of the medicament. In some embodiments, the processor is within the communication accessory 42.

The sensor assembly 62 may be configured to detect the volume of fluid or medicament in the medicament chamber. In one embodiment, the sensor assembly 62 may include a sensor configured to optically detect the position of the plunger 28 in the medicament chamber. In another embodiment, the sensor assembly 62 optically detects the presence or absence of liquid in the reservoir through the shifting of a mark on the far side of the reservoir due to the different indexes of refraction of a liquid and air.

Referring to FIGS. 2 and 6, the sensor assembly 62 may include a bolus delivery button sensor 66 (FIG. 6) to detect the position of the bolus delivery button 36 (FIG. 2) and thus detect when the bolus delivery button 36 is actuated. The bolus delivery button 36 may include a bolus delivery button indicator 64 (FIG. 2) extending to or near the top surface of the housing 24 to interact with bolus delivery button sensor 66.

In one embodiment, the bolus delivery button sensor 66 is an optical sensor and the bolus delivery button indicator 64 is a pigmented area. In another embodiment, the bolus delivery button sensor 66 is magnetically sensitive (Hall effect or reed switch) and the bolus delivery button indicator 64 is a magnet. In another embodiment, the bolus delivery button sensor 66 is an optical interrupt device and the bolus delivery button indicator 64 passes into the optical interrupt gap or deflects a spring tab into the gap. In another embodiment, the bolus delivery button sensor 66 has electrical contacts and the bolus delivery button indicator 64 is a conductive area. In another embodiment, the bolus delivery button sensor 66 is a switch and the bolus delivery button indicator 64 is an extension of the bolus delivery button that strikes the switch. In another embodiment, the bolus delivery button sensor 66 is a membrane or elastomeric switch with a reversibly displaceable portion that collapses under force and electrically connects contacts under the collapsed portion(s) and returns to its initial shape breaking contact when the force is removed. In another embodiment, the bolus delivery button sensor 66 is a detect micro switch such as a Panasonic ESE16J001. In another embodiment, the bolus delivery button sensor 66 is a tactile switch. In one embodiment, at least one of the bolus delivery button sensor 66 and the bolus delivery button indicator 64 is coated with a waterproofing material (e.g., Parylene or polyurethane). In one embodiment, at least one of the bolus delivery button sensor 66 and the bolus delivery button indicator 64 is covered with a hydrophobic coating. In one embodiment, at least one of the bolus delivery button sensor 66 and the bolus delivery button indicator 64 is covered with a waterproofing membrane which allows a switch to be activated through the membrane. In one embodiment, at least one of the bolus delivery button sensor 66 and the bolus delivery button indicator 64 is indirectly actuated by a lever arm or spring that is deflected by contact with bolus delivery button indicator 64.

Still referring to FIGS. 2 and 6, the sensor assembly 62 may include a needle deploy button sensor 68 to detect the position of the needle deploy button 34. In one embodiment, the needle deploy button sensor 68 is an optical sensor that can differentiate wavelengths of light and the needle deploy button 34 is a pigmented with a selected color. The needle deploy button sensor 68 may detect the absence of the needle deploy button 34 when the needle deploy button 34 is depressed, thereby indicating that the needle has been deployed. In another embodiment, the needle deploy button sensor 68 is an optical sensor that can detect light emitted by a source in the communication accessory 42 and reflected off of the needle deploy button 34 when the needle 30 is in the retracted position.

In another embodiment, the needle deploy button sensor 68 is an optical sensor that can detect light of a specific wavelength range that is emitted by the fluorescence of a pigment in the needle button when excited by a light of a different wavelength from a source in the communication accessory 42 when the needle 30 is in the retracted position. In some embodiments, the wavelength of the emitted light is an indication of the model of the delivery device. In another embodiment, the needle deploy button sensor 68 is a detect micro switch actuated by part of the needle deploy button 34. In another embodiment, the needle deploy button sensor 68 is a tactile switch actuated by part of the needle deploy button 34.

The sensor assembly 62 may include a needle position sensor to detect a position of the needle 30. The needle position sensor may be an optical sensor, a tactile sensor, or a detect micro switch sensor.

In one embodiment, the needle deploy button sensor 68 is coated with a waterproofing material (e.g., Parylene or polyurethane). In one embodiment, the needle deploy button sensor 68 is covered with a hydrophobic coating. In one embodiment, the needle deploy button sensor 68 is covered with a waterproofing membrane molded or formed to allow the switch to be activated through the membrane.

The needle deploy button sensor 68 may be activated by an actuator 70 (e.g., a lever arm) which may be deflected when it is contacted by a protrusion on the needle deploy button 34. In one embodiment, the needle deploy button sensor 68 is a Hall effect or reed switch and is indirectly actuated by a magnet coupled to the actuator 70 that is a resilient flexing member that deflects under force from the needle deploy button 34 or an intermediate element and returns to a less deformed position when the needle deploy button 34 is depressed to the needle deployed position.

In one embodiment, the needle deploy button sensor 68 is an optical interrupt switch that is triggered by an interference member (not shown) that moves into, or out of, a light path to trigger the needle deploy button sensor 68. In one embodiment, the interference member and the needle deploy button 34 are a unitary construct. In another embodiment, the interference member and the actuator 70 are a unitary construct. In another embodiment, the needle deploy button 34 contacts and moves the interference member when the needle deploy button 34 is moved by a user. The interference member may be moved by an intermediate piece that is moved (e.g., translated or rotated) by the needle deploy button 34.

Figure 10:
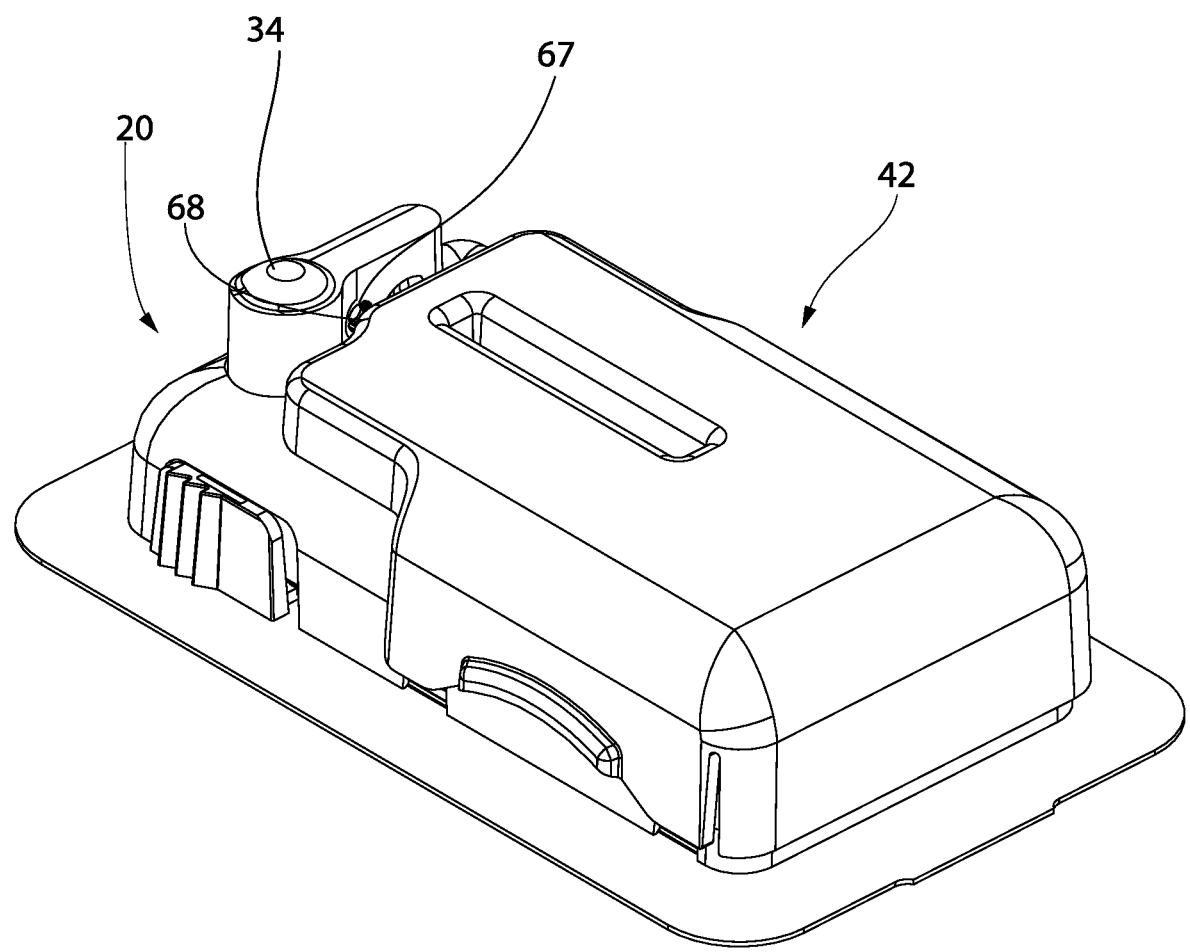
FIG. 10 is a top trimetric view of the communication accessory of FIG. 1.
Figure 11:
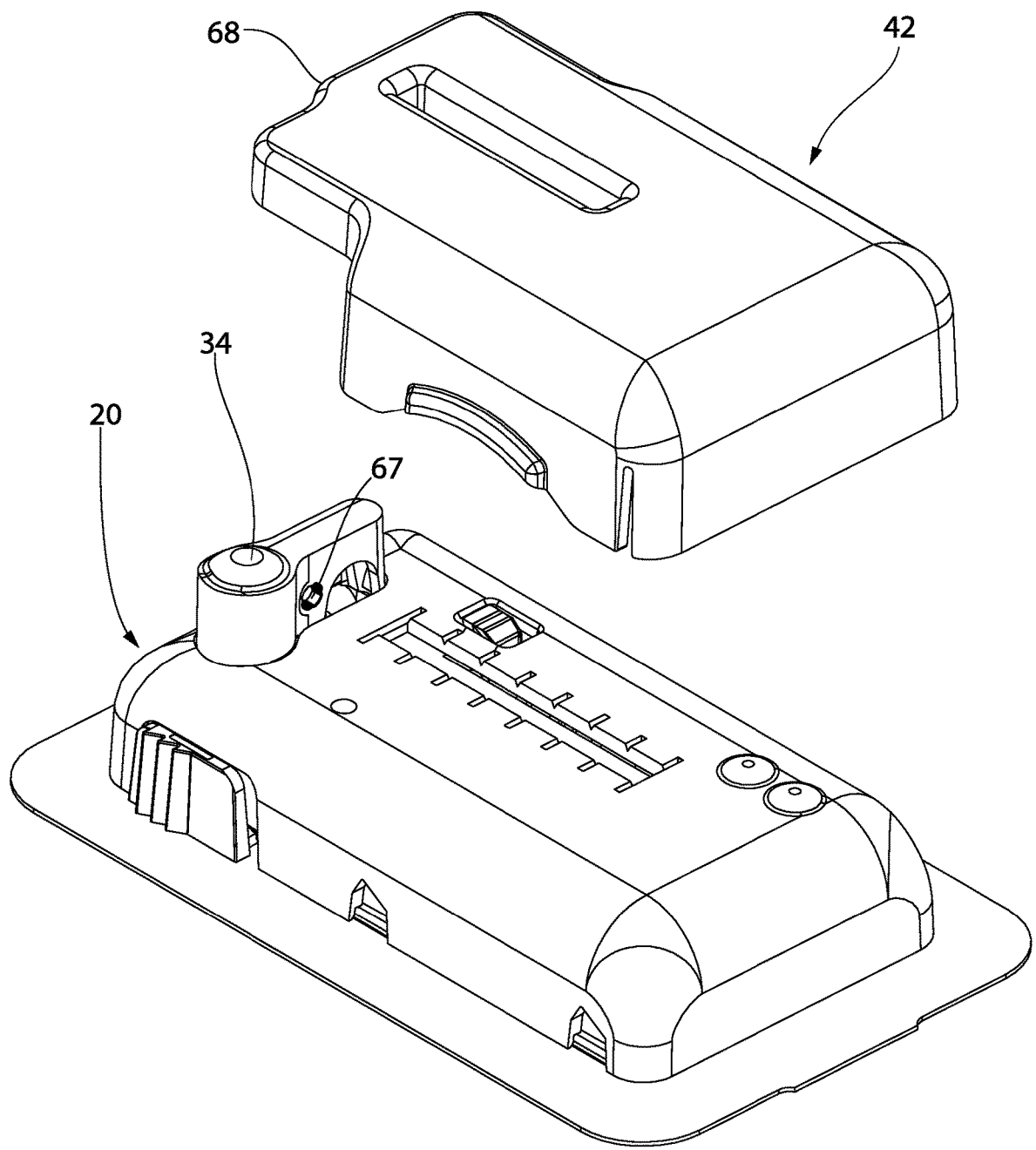
FIG. 11 is a top trimetric view of the communication accessory of FIG. 1 detached from the delivery device.

Referring to FIGS. 10-11, the needle deploy button sensor 68 may be a magnetically sensitive sensor (Hall Effect or reed switch). A magnet 67 may be fixed to the needle deploy button 34. The needle deploy button sensor 68 may detect a change in the presence of the magnet 67 when the needle deploy button 34 moves from the needle retracted position to the needle extended position. In one embodiment, the magnet 67 is positioned so that the needle deploy button sensor 68 senses the presence of the magnet 67 when the needle deploy button 34 is in the needle retracted position. The magnet 67 may be moved with the needle deploy button 34 out of range of the magnetic needle deploy button sensor 68 thus changing the state of the needle deploy button sensor 68 and allowing the communication accessory 42 to determine the position of the needle deploy button 34. In another embodiment, the magnet 67 is out of range of the needle deploy button sensor 68 prior to the needle being deployed and comes into range when the needle is deployed. In some embodiments, the needle deploy button sensor 68 detects the direction of a magnetic field of the magnet 67 and the orientation of the magnet 67 is indicative the model of the delivery device.

In one embodiment, the needle deploy button sensor 68 has electrical conductors configured to be electrically connected to a conductive area of the needle deploy button 34. The electrical connection may be established when the needle deploy button 34 is in the needle retracted position, and the electrical connection may be broken when the needle deploy button 34 is in the needle extended position indicating the needle deploy button 34 is depressed.

In another embodiment, the needle deploy button sensor 68 is a capacitive sensor and senses a conductive area of the needle deploy button 34. The needle deploy button sensor 68 detects the change in capacitance when the needle deploy button 34 is moved to the needle deployed position indicating a change in the position of the needle deploy button 34. The sensor assembly 62 may include a motion sensor to track activity of the user. The sensor assembly 62 may include a position sensor to detect user location.

Referring to FIG. 6, the communication accessory 42 may include a circuit board 78 coupled to a battery 80. The circuit board 78 may include the electronic components necessary for the communication accessory 42 to receive one or more signals from the sensor assembly 62 and communicate with an external device. The battery 80 (such as a CR1620.TS) may be electrically coupled to the circuit board 78 by one or more connectors 82. In one embodiment, the battery 80 is fixed to the communication accessory 42. In another embodiment, the battery 80 may be decoupled from the communication accessory 42 as desired. The battery 80 may be rechargeable via a wired charger or through inductive coupling. The circuit board 78 and/or the battery 80 may be coated with a water resistant coating (e.g., Parylene or a dipped or sprayed acrylic or polyester).

Figure 7:
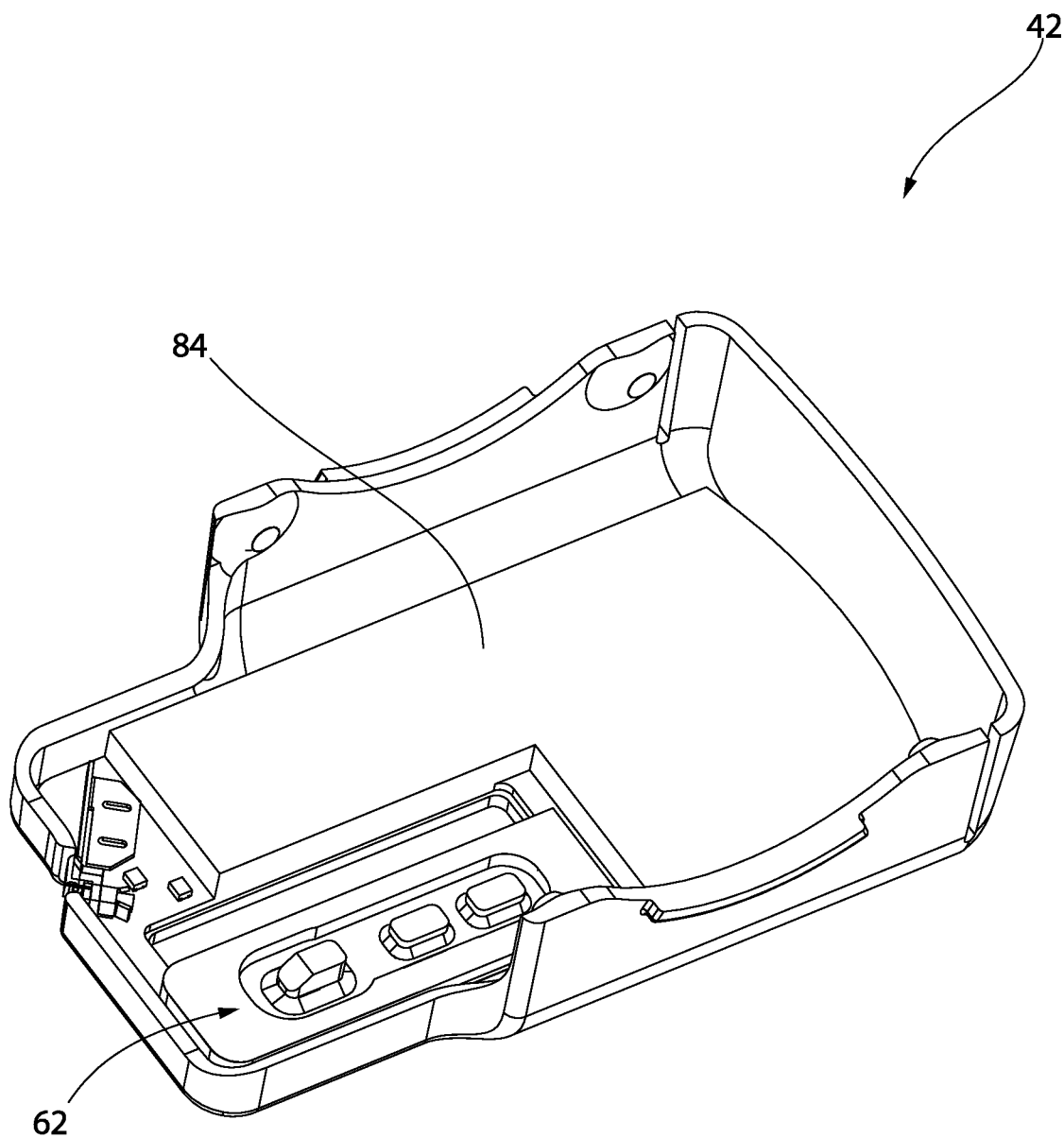
FIG. 7 is a bottom trimetric view of the communication accessory of FIG. 5 with a barrier coupled to the communication accessory.

Referring to FIG. 7, a cover such as an over-molding 84 may be coupled to the communication accessory 42 such that the over-molding forms a barrier on the circuit board 78 and battery 80. The over-molding 84 may be water resistant. The over-molding 84 may be waterproof. The over-molding 84 may provide a barrier to moisture, heat, dust, dirt, or air. In one embodiment, the over-molding 84 is formed from a low temperature thermoplastic (e.g., polyamide adhesive thermoplastic). In another embodiment, the over-molding 84 is formed from cast silicone, epoxy, or other polymer. In another embodiment, the over molding is a liquid potting material of epoxy, silicone or urethane poured into the communication accessory after assembly up to less than the top surface of the sensors and allowed to harden. At least a portion of the communication accessory 42 may be formed from the same or a similar thermoplastic as the over-molding 84.

Figure 8:
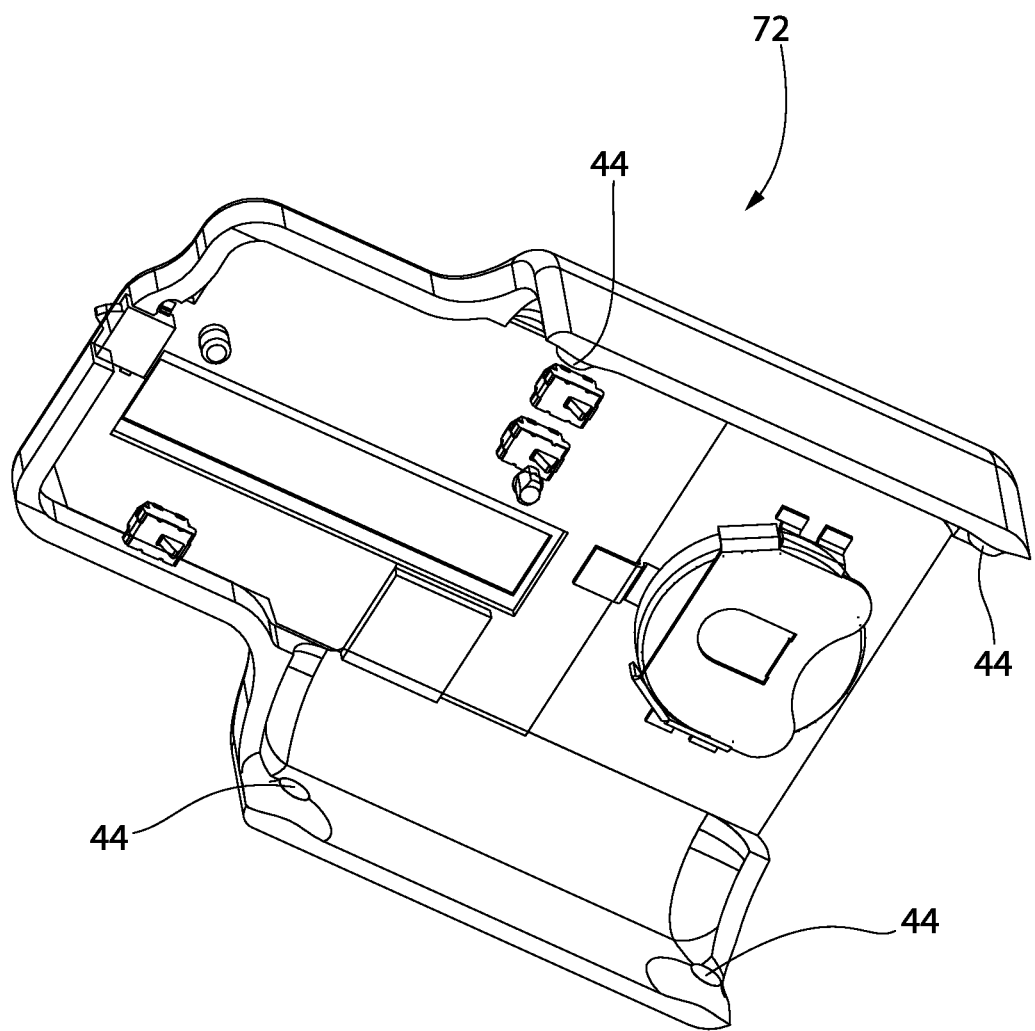
FIG. 8 is a bottom trimetric view of a communication accessory in accordance with another exemplary embodiment of the present invention.
Figure 9:
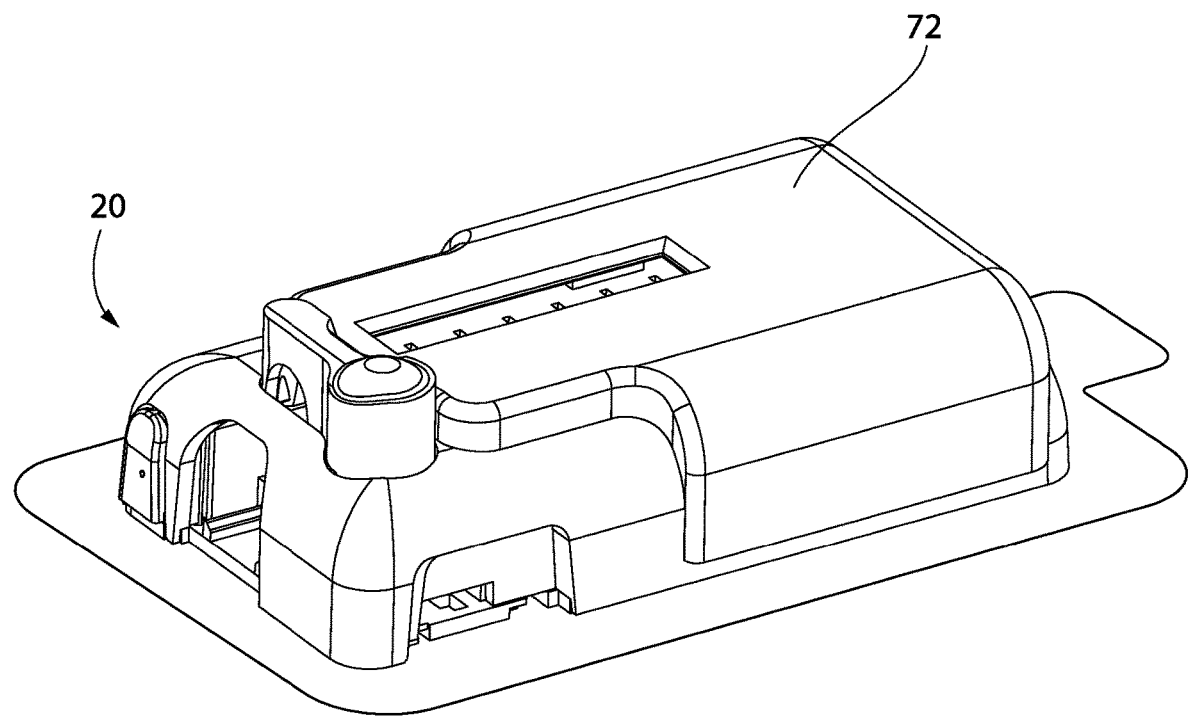
FIG. 9 is a trimetric view of the communication accessory of FIG. 8 coupled to the delivery device of FIG. 2.

Referring to FIGS. 8-9, another exemplary embodiment of a communication accessory, generally designated 72, is shown. The communication accessory 72 is similar to communication accessory 42, but the communication accessory 72 does not include an end wall. The sensor assembly 62 may function best when the communication accessory 72 is properly positioned on the delivery device 20. The end wall 52 of the communication accessory 42 (see FIG. 5) may prevent misalignment of the communication accessory 42 on the delivery device 20.

The communication accessory 72 may include non-symmetric accessory engagement features 44 and the delivery device 20 may include non-symmetric housing engagement features 46 to prevent misalignment of the communication accessory 72 and the delivery device 20. In one embodiment, the accessory engagement features 44 may be protrusions on one side of the communication accessory and recesses on the other side such that the communication accessory 72 can only be coupled to the delivery device 20 in one orientation.

Figure 12:
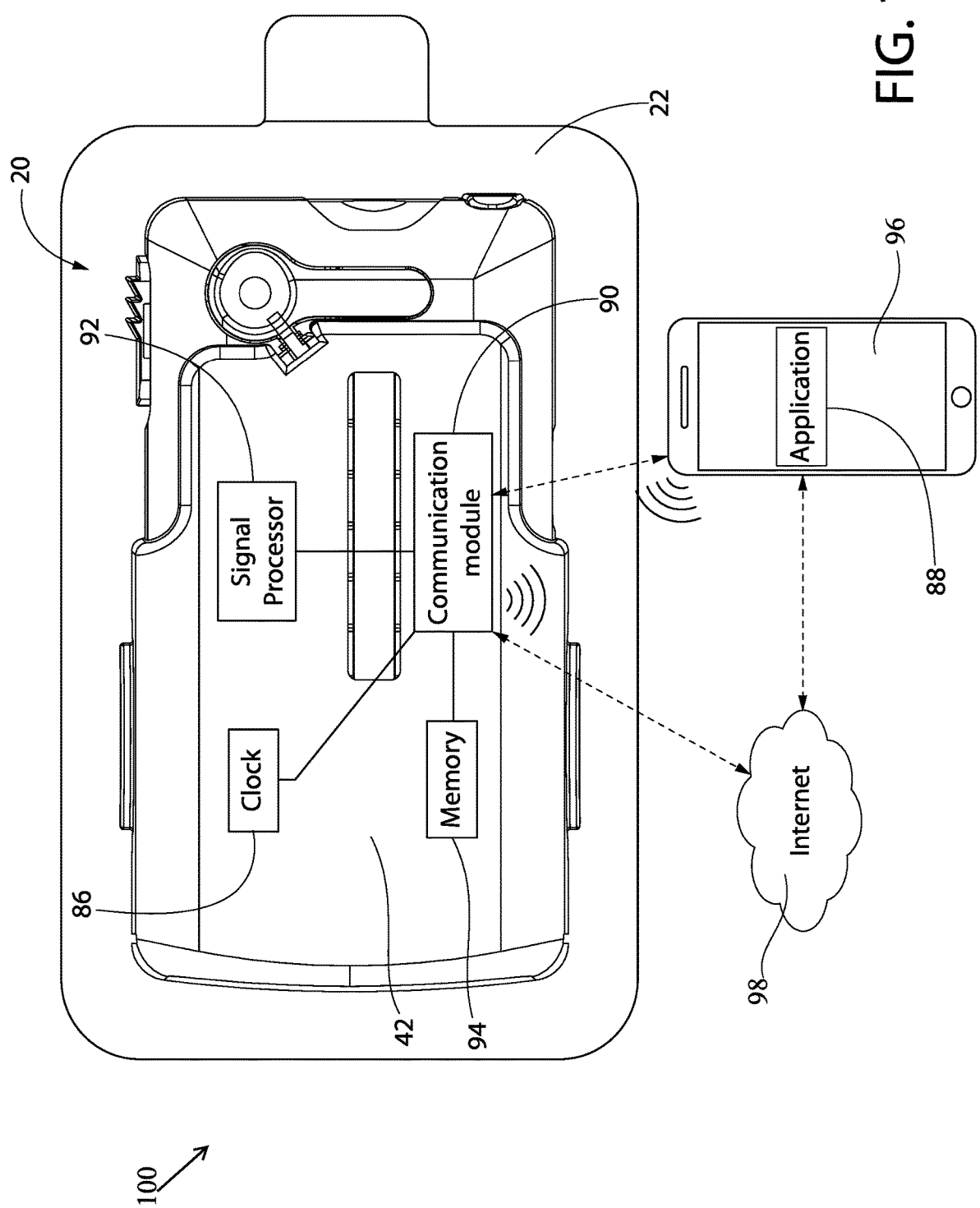
FIG. 12 is a schematic illustration of an ambulatory drug delivery system including the communication accessory of FIG. 1.

Referring to FIG. 12, an ambulatory drug delivery system 100 may include the communication accessory 42 may include a communication module 90 configured to communicate (e.g., via Bluetooth, Bluetooth Low Energy, text message, email, or the internet) with an external device 96 (e.g., cellular phone, mobile device, or computer). The communication accessory 42 may send information to an external device any time a signal is received from the sensor assembly 62. The communication accessory 42 or external device 96 may include a signal processor 92 configured to receive a first signal from the sensor assembly 62. The communication accessory 42 may include memory 94 configured to store information (e.g., information from the first signal). The communication accessory 42 may transmit a second signal (e.g., information from the first signal or stored information) to the external device 96 (e.g., a mobile device or computer) when the communication accessory 42 is within range or connected to the external device.

The communication module 90 may receive a signal from at least one of a clock 86, the software application 88, the signal processor 92, or the memory 94. The communication module 90 may be configured to communicate with external device 96 via internet 98, intranet, or local area network. The communication module 90 may send information to a cloud based server via the internet 98 and a third party may access the information on the cloud based server.

In one embodiment, the memory of the communication accessory 42 has sufficient storage to save all the data collected by the accessory over a time range of about 1 day, about 2 days, about 3 days, about 4 days, about 5 days, about 6 days, about 7 days, about 2 weeks, about 3 weeks, about 1 month, about 2 months, about 3 months, about 4 months, about 5 months, about 6 months, about 1 month to 3 months, about 2 months to about 4 months, about 3 months to about 5 months, or about 4 months to about 6 months. The communication accessory 42 may be paired to the external device. The communication accessory 42 may transmit all the stored data to the external device when the communication accessory is paired to the external device. The communication accessory 42 may transmit all the stored data to the external device any time a new external device is paired to the communication accessory. The communication accessory 42 may transmit to the external device only the data which has been saved since the last time the communication accessory was paired to the external device.

Still referring to FIG. 12, the communication accessory 42 may include the clock 86 (e.g, an internal clock or timer) that starts when the communication accessory is placed on a delivery device 20. The communication accessory 42 may transmit timing information related to a sensed action (e.g., time when a bolus was delivered, time when the dose began to be delivered from the medicament chamber 26). The external device which the communication accessory 42 pairs to may include its own clock that is synchronized with actual time so software in the external device (e.g., a software application 88) can calculate the actual time of each action sensed by the communication accessory even if the communication accessory 42 merely indicates how much time has elapsed since an event. The software application 88 may be stored locally on the external device. The software application may be stored remotely on one or more servers and the external device may access the software application through a communication network (e.g., interne, intranet, or local area network). The software application may be partially stored on the external device and partially stored in one or more remote servers.

The software application 88 on the device may display a list of all the actions sensed by the communication accessory 42 during a period from when the accessory was placed on the delivery device 20 until the communication accessory 42 senses the needle deploy button 34 returns to the needle retracted position. The software application 88 on the device may display a list of all the actions sensed by the communication accessory 42 during a period from when the accessory was placed on the delivery device 20 on a specified day until the communication accessory 42 senses the needle deploy button 34 returns to the needle retracted position.

The software application 88 on the device may display the number of bolus deliveries left in the delivery device 20 by subtracting the number of bolus presses from the preprogrammed total number available. The software application 88 on the device may display the total amount of fluid or medicament delivered during a period from when the accessory was placed on the delivery device 20 until the communication accessory 42 senses the needle deploy button 34 returns to the needle retracted position.

The software application 88 on the device may allow the user to enter additional data such as additional medication taken or blood glucose measurements. The software application 88 on the device may allow a user to select which information is displayed on the device. The software application 88 on the device may display user entered data along with data captured by the communication accessory 42. The software application 88 on the device may display a low battery status when a low battery state is detected and transmitted by the communication accessory 42.

The software application 88 on the device may display the use time remaining for the delivery device 20. The software application 88 may calculate the use finish time based on the time the needle deploy button 34 activation was sensed and the preprogrammed expected delivery time of the delivery device 20. The software application 88 on the device may provide an alarm when the preprogrammed design life of the delivery device 20 has expired. The alarm may be audible, tactile (e.g., vibration), or visible. The software application 88 on the device may activate the alarm if the communication accessory 42 has not sensed the bolus delivery button 36 being pressed for a selected interval. The software application 88 on the device may activate the alarm if the communication accessory 42 has not sensed that the communication accessory 42 has been secured to a delivery device 20 for a selected interval. The software application 88 on the device may provide an alarm when an error state has been detected.

The software application 88 on the device may be configured to communicate (e.g., through e-mail or text message) the data stored in the software application to a manually entered or preprogrammed electronic address through the device connection to a data connection network (e.g., the internet). The software application 88 on the device may be configured to communicate (e.g., through e-mail or text message) a formatted report containing the data stored in the software application to a manually entered or preprogrammed electronic address through the device connection to a data connection network (e.g., the internet).

In one embodiment, the delivery device 20 and communication accessory 42 are included in a kit. The kit may include a plurality of delivery devices 20. The communication accessory 42 may be configured to be releasably coupled to each of the plurality of delivery devices 20. The communication accessory 42 may be resettable such any saved data is erased or written over each time the communication accessory 42 is coupled to a new delivery device. The communication accessory 42 may save data to compare trends across the plurality of delivery devices 20.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. The words "right", "left", "lower" and "upper" designate directions in the drawings to which reference is made. The words "inwardly" and "outwardly" refer to directions toward and away from, respectively, the geometric center of the delivery device and communication accessory. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A medicament delivery assembly comprising:
    a delivery device configured to deliver medicament to a user, the delivery device comprising:
        a housing;
        a bolus delivery button and a bolus delivery button indicator coupled to the housing;
        a medicament chamber positioned within the housing and configured to hold a medicament;
        a plunger positioned within the medicament chamber and configured to move relative to the medicament chamber to expel the medicament from the medicament chamber;
        a needle configured to couple to the medicament chamber such that, in use, the medicament flows through the needle from the medicament chamber to the user; and
    a communication accessory releasably coupled to the delivery device and comprising one or more sensors configured to sense a condition of the delivery device,
    wherein the one or more sensors are configured to sense activation of the bolus delivery button via the bolus delivery button indicator from the delivery device,
    wherein the communication accessory is configured to receive a first signal from the one or more sensors and send a second signal to an external device,
    wherein the housing of the delivery device includes a window configured to allow a user to observe the medicament chamber through the housing, and
    wherein the communication accessory comprises an opening aligned with the window of the delivery device such that a user may observe the medicament chamber through the opening when the communication accessory is coupled to the delivery device.

2. The medicament delivery assembly of claim 1, wherein the one or more sensors are configured to sense delivery of a dose of medicament from the medicament chamber.

3. The medicament delivery assembly of claim 1, wherein the plunger is moveable relative to the medicament chamber and the one or more sensors are configured to sense a position of the plunger in the medicament chamber.

4. The medicament delivery assembly of claim 1, wherein the needle is moveable relative to the delivery device from a retracted position to an extended position and the one or more sensors are configured to sense a position of the needle.

5. The medicament delivery assembly of claim 1, wherein the delivery device further comprises:
 a needle deploy button configured to move the needle between a retracted position and an extended position wherein the one or more sensors includes a sensor configured to sense activation of the needle deploy button.

6. The medicament delivery assembly of claim 1, wherein the communication accessory includes a processor configured to determine at least one of a number of boluses delivered, a number of boluses remaining, delivery of a dose of medicament from the medicament chamber, and a number of doses of medicament remaining in the medicament chamber.

7. The medicament delivery assembly of claim 1, wherein the external device includes a processor configured to determine at least one of a number of boluses delivered, a time when the bolus was delivered, a number of boluses remaining, a volume of medicament delivered from the medicament chamber, a number of doses delivered from the medicament chamber, a number of doses of medicament remaining in the medicament chamber, and an expected time of medicament chamber emptying based on the second signal.

8. The medicament delivery assembly of claim 1, wherein the delivery device is non-electronic.

9. The medicament delivery assembly of claim 1, wherein each of the one or more sensors are configured to sense one of a plurality of conditions of the delivery device.

10. The medicament delivery assembly of claim 1, wherein the external device includes a software application configured to display indicia related to the condition sensed by the one or more sensors.

11. The medicament delivery assembly of claim 1, wherein the one or more sensors are part of a sensor assembly.

12. The medicament delivery assembly of claim 1, wherein the delivery device is a non-electronic delivery device, and wherein the one or more sensors includes an electronic sensor configured to sense a condition of the non-electronic delivery device.

13. The medicament delivery assembly of claim 1, wherein the delivery device is selected from a plurality of delivery device models, and
 wherein the one or more sensors are configured to sense the model of the selected delivery device.

14. The medicament delivery assembly of claim 1, wherein the one or more sensors includes at least one of a magnetic sensor, a capacitive sensor, a pushbutton switch, a membrane switch, a molded elastomeric switch, a tactile switch, and an optical sensor.

15. The medicament delivery assembly of claim 1, wherein the communication accessory includes memory and the communication accessory is configured to store the first signal in the memory as a saved signal.

16. The medicament delivery assembly of claim 1, wherein the communication accessory is configured to send the second signal to the external device via a wireless connection.

17. The medicament delivery assembly of claim 1, wherein the delivery device is an electronic delivery device that does not transfer use information.

18. The medicament delivery assembly of claim 1, wherein the bolus delivery button indicator comprises an opening in a housing of the delivery device.

19. The medicament delivery assembly of claim 1, wherein the delivery device comprises one or more additional indicators which are configured to be sensed by the communication device for allowing the communication device to identify a model or configuration of the delivery device.

20. The medicament delivery assembly of claim 19, wherein each additional indicator comprises a protrusion.

21. The medicament delivery assembly of claim 1,
 wherein the delivery device further comprises a plurality of engagement features for allowing the communication accessory to be releasably coupled to the delivery device, wherein the plurality of engagement features comprises:
 a first pair of engagement features on a first side of the delivery device; and
 a second pair of engagement features on a second side of the delivery device, wherein the second side is opposite the first side.

22. The medicament delivery assembly of claim 21, wherein each of the plurality of engagement features comprises a recess.

23. A medicament delivery assembly comprising:
 a non-electronic delivery device configured to deliver medicament to a user, the delivery device comprising:
  a housing;
  a medicament chamber positioned within the housing and configured to hold a medicament;
  a plunger positioned within the medicament chamber and configured to move relative to the medicament chamber to expel the medicament from the medicament chamber;
  a needle configured to couple to the medicament chamber such that, in use, the needle is moveable from a retracted position to an extended position, wherein medicament flows through the needle from the medicament chamber to the user when the needle is in the extended position;
  a needle deploy button configured to move the needle between the retracted position and the extended position;
  a bolus delivery button configured to deliver a bolus of medicament to the user through the needle and a bolus delivery button indicator, both the bolus delivery button and the bolus delivery button indicator being coupled to the housing;
 a communication accessory releasably coupled to the non-electronic delivery device and comprising one or more sensors configured to sense a condition of the delivery device and provide a signal related to the sensed condition, the one or more sensors comprising:
  a sensor configured to sense activation of the bolus delivery button via the bolus delivery button indicator from the delivery device,
 wherein the communication accessory is configured to receive a signal from at least one of the one or more sensors and to send a second signal related to the received signal to an external device,
 wherein the external device includes a software application configured to display indicia related to the condition sensed by the one or more sensors,
 wherein the delivery device includes a window configured to allow a user to observe the medicament chamber through the housing, and wherein the communication accessory comprises an opening aligned with the window of the delivery device such that a user may observe the medicament chamber through the opening when the communication accessory is coupled to the delivery device.

24. The medicament delivery assembly of claim 23, wherein the software application is further configured to determine at least one of a model of the delivery device, a number of boluses delivered by the medicament delivery device, a number of boluses remaining in the medicament delivery device, a volume of medicament delivered from the medicament delivery device, a number of doses of medicament delivered from the medicament delivery device, a volume of medicament remaining in the medicament delivery device, a number of doses of medicament remaining in the medicament delivery device, a time the needle was deployed by the medicament delivery device, and an expected time when a medicament chamber in the medicament delivery device will be empty based on the second signal.

25. A medicament delivery assembly comprising:
   a delivery device configured to deliver medicament to a user, the delivery device comprising:
      a bolus delivery button and a bolus delivery button indicator;
      a medicament chamber configured to hold a medicament;
      a plunger configured to move relative to the medicament chamber to expel the medicament from the medicament chamber; and
      a needle coupled to the medicament chamber, wherein medicament flows through the needle from the medicament chamber to the user; and
   a communication accessory releasably coupled to the delivery device; and
   one or more sensors configured to sense a condition of the delivery device, wherein the one or more sensors are configured to sense activation of the bolus delivery button via the bolus delivery button indicator from the delivery device,
wherein the communication accessory is configured to receive a first signal from the one or more sensors and send a second signal to an external device,
wherein the delivery device further comprises a housing, and a window a user for allowing a user to observe the medicament chamber through the housing, and
wherein the communication accessory comprises an opening aligned with the window of the delivery device such that a user may observe the medicament chamber through the opening when the communication accessory is coupled to the delivery device.

* * * * *